(12) United States Patent
Sodickson et al.

(10) Patent No.: US 11,169,097 B2
(45) Date of Patent: Nov. 9, 2021

(54) DEVICE AND METHOD FOR HARMONIC ELECTROMAGNETIC SPECTROSCOPY

(71) Applicant: NEW YORK UNIVERSITY, New York, NY (US)

(72) Inventors: Daniel K. Sodickson, Larchmont, NY (US); Martijn Anton Hendrik Cloos, Long Island City, NY (US)

(73) Assignee: New York University, New York, NY (US)

( * ) Notice: Subject to any disclaimer, the term of this patent is extended or adjusted under 35 U.S.C. 154(b) by 83 days.

(21) Appl. No.: 16/725,360

(22) Filed: Dec. 23, 2019

(65) Prior Publication Data

US 2020/0209169 A1    Jul. 2, 2020

Related U.S. Application Data

(60) Provisional application No. 62/785,146, filed on Dec. 26, 2018.

(51) Int. Cl.
| | |
|---|---|
| *G01R 27/04* | (2006.01) |
| *G01R 27/32* | (2006.01) |
| *G01N 22/00* | (2006.01) |
| *G01N 27/02* | (2006.01) |
| *G01N 22/04* | (2006.01) |
| *G01N 29/02* | (2006.01) |
| *A61B 5/00* | (2006.01) |

(52) U.S. Cl.
CPC ............. *G01N 22/00* (2013.01); *G01N 22/04* (2013.01); *G01N 27/02* (2013.01); *G01N 27/023* (2013.01); *G01N 27/026* (2013.01); *G01N 29/022* (2013.01); *A61B 5/0031* (2013.01); *A61B 2560/0219* (2013.01)

(58) Field of Classification Search
CPC ...... G01N 22/00; G01N 27/023; G01N 22/04; G01N 27/02; G01N 27/026; G01N 29/022; G01N 22/02; A61B 5/0031; A61B 2560/0219
USPC .......... 324/76.11–76.83, 459, 600, 629, 633, 324/652, 655, 658, 675, 708
See application file for complete search history.

(56) References Cited

U.S. PATENT DOCUMENTS

| | | | |
|---|---|---|---|
| 2006/0158172 A1* | 7/2006 | King ...................... | G01V 15/00 324/66 |
| 2015/0192627 A1* | 7/2015 | Rubesa ................ | G01N 37/005 324/76.51 |
| 2016/0123971 A1* | 5/2016 | Taicher .................. | G01N 24/08 436/501 |
| 2019/0150370 A1* | 5/2019 | Engle ..................... | B01J 19/129 |

(Continued)

*Primary Examiner* — Raul J Rios Russo
(74) *Attorney, Agent, or Firm* — Foley & Lardner LLP (57) ABSTRACT

An apparatus for non-destructive testing of a sample includes a sample holder configured to contain or support the sample; an exciter configured to generate an oscillating electromagnetic field across the sample that operates with at least one predetermined excitation frequency; a receiver configured to detect harmonic electromagnetic signals resulting from induced electromagnetic fields oscillating with at least one frequency that is not equal to the at least one predetermined excitation frequency; a recorder configured to record the harmonic electromagnetic signals; and a processor programmed to construct an induced harmonic electromagnetic spectrum based on the harmonic electromagnetic signals.

20 Claims, 10 Drawing Sheets

(56) References Cited

U.S. PATENT DOCUMENTS

2019/0152812 A1\* 5/2019 Engle ................ C02F 1/487
2020/0278308 A1\* 9/2020 Kalenychenko ... G01N 23/2273

\* cited by examiner

DEVICE AND METHOD FOR HARMONIC ELECTROMAGNETIC SPECTROSCOPY

CROSS-REFERENCE TO RELATED APPLICATIONS

The present application claims the benefit of priority under 35 U.S.C. § 119(e) to U.S. Provisional Application No. 62/785,146 filed Dec. 26, 2018, the entire content of which is incorporated herein by reference.

BACKGROUND

The present disclosure relates generally to a system and method of non-destructive sample characterization. More specifically, the present disclosure relates to a system and method for characterizing samples using remote induction and detection of harmonic electromagnetic signals.

Non-destructive testing techniques are used to evaluate the properties of a sample, including flaws in the sample, without destroying the sample. When the non-destructive testing is completed, the sample can still be used for its intended purpose. Many different natural phenomena can be harnessed to create methods to non-destructively test samples of various sorts. For example, non-destructive testing techniques include Acoustic Emission Testing (AE), Electromagnetic Testing (ET), Guided Wave Testing (GW), Ground Penetrating Radar (GPR), Laser Testing Methods (LM), Leak Testing (LT), Magnetic Flux Leakage (MFL), Microwave Testing, Liquid Penetrant Testing (PT), Magnetic Particle Testing (MT), Neutron Radiographic Testing (NR), Radiographic Testing (RT), Thermal/Infrared Testing (IR), Ultrasonic Testing (UT), Vibration Analysis (VA) and Visual Testing (VT). Non-destructive testing techniques are highly valuable tools in research, quality control, trouble shooting, and diagnostics.

Many of the non-destructive testing techniques are expensive or require a bulky apparatus. For example, performing NMR or MM generally requires superconducting magnets or other bulky equipment.

A need exists for improved technology, namely, for an affordable non-destructive testing technique that can be applied to a wide range of samples across different fields of research.

SUMMARY OF THE INVENTION

At least one embodiment relates to an apparatus for non-destructive testing of a sample including a sample holder configured to fully or partially contain or support the sample; an exciter configured to generate an oscillating electromagnetic field across the sample that operates with at least one predetermined excitation frequency; a receiver configured to detect harmonic electromagnetic signals resulting from induced electromagnetic fields oscillating with at least one frequency that is not equal to the at least one predetermined excitation frequency; a recorder configured to record the harmonic electromagnetic signals; and a processor programmed to construct an induced harmonic electromagnetic spectrum based on the harmonic electromagnetic signals. In general, the excitation may occur at a single predetermined frequency, or a plurality of different frequencies (i.e., the excitation may be varied to construct a plurality of induced harmonic electromagnetic spectra).

At least another embodiment relates to a method of generating a harmonic electromagnetic spectrum for non-destructive testing of a sample. The method includes placing a sample in a sample holder or otherwise bringing the sample into the vicinity of a testing apparatus; generating an oscillating electromagnetic field across the sample that operates with at least one predetermined excitation frequency; detecting harmonic electromagnetic signals resulting from induced electromagnetic fields oscillating with at least one frequency that is not equal to the at least one predetermined excitation frequency; and constructing an induced harmonic electromagnetic spectrum based on the harmonic electromagnetic signals. In general, the predetermined excitation may occur at a single frequency, or a plurality of different frequencies (i.e., the excitation may be varied to construct a plurality of induced harmonic electromagnetic spectra).

At least another embodiment relates to a method of generating a harmonic electromagnetic spectrum for non-destructive testing of a sample. The method includes placing a sample in a sample holder or otherwise bringing the sample into the vicinity of a testing apparatus; collecting a first set of measurements by generating an excitation field across the sample that operates at a first single predetermined frequency, detecting harmonic electromagnetic signals resulting from induced electromagnetic fields oscillating at least one frequency that is not equal to the first single predetermined frequency, and constructing a first induced harmonic electromagnetic spectrum based on the harmonic electromagnetic signals; and collecting a second set of measurements by generating an excitation field across the sample that operates at a second single predetermined frequency different from the first single predetermined frequency, detecting harmonic electromagnetic signals resulting from induced electromagnetic fields oscillating at least one frequency that is not equal to the second single predetermined frequency, and constructing a second induced harmonic electromagnetic spectrum based on the harmonic electromagnetic signals.

At least another embodiment relates to a method of generating a harmonic electromagnetic spectrum for non-destructive testing of a sample. The method includes placing a sample in a sample holder or otherwise bringing the sample into the vicinity of the testing apparatus; generating a time-varying electromagnetic field across the sample; detecting distortions of the waveform of the electromagnetic field; and constructing an induced harmonic electromagnetic spectrum based on the detected waveform distortions.

In any of the embodiments described above, "bringing the sample into the vicinity of the testing apparatus," may include bringing the testing apparatus to the sample, for example, in a handheld or wearable configuration, as opposed to surrounding the sample by the testing apparatus in a sample holder.

This summary is illustrative only and is not intended to be in any way limiting.

BRIEF DESCRIPTION OF THE DRAWINGS

The disclosure will become more fully understood from the following detailed description, taken in conjunction with the accompanying figures, wherein like reference numerals refer to like elements, in which:

FIG. 8 illustrates an example of using the harmonic electromagnetic spectrometer of FIG. 1 to evaluate an organic tissue sample. When the ions in a cell are not constrained by nearby structures (e.g., in the large neuronal fiber cross-section shown at top), the ions will generate a response field at the same frequency as the incident field. However, if the ions' motion is constrained by microstructural features in the sample (e.g., in the small axon at bottom), the induced motion pattern of the ions will be truncated, resulting in truncated reaction fields, with substantial frequency content at harmonics of the incident field frequency. The ensemble of resulting harmonics can be induced and measured to obtain a harmonic electromagnetic spectrum.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

When the motion of charged particles in a conductive medium is unrestricted, a reaction field is created that oscillates at the same frequency as the incident fields. However, local variations in the sample may alter the motion pattern, leading to complex time-dependent reaction fields, with components at frequencies other than the frequency of the incident field. The presence of such reaction fields can be interpreted as a marker of certain microscopic features. For example, dense cellular membranes can impede the motion of ions in organic tissues. When an oscillating electric field is applied, the reaction fields produced by these constrained ions may be truncated or saturated. In other words, the observation of truncated reaction fields can be interpreted as evidence of microscopic restrictions in the local ion environment.

Referring to the figures in general, the present disclosure relates to a system and method for non-destructive testing of samples using remote induction and detection of harmonic electromagnetic signals. In particular, the present disclosure relates to a system and method for non-destructive sample characterization based on harmonics in the electromagnetic reaction fields produced by charged particles in a complex medium.

Figure 1:
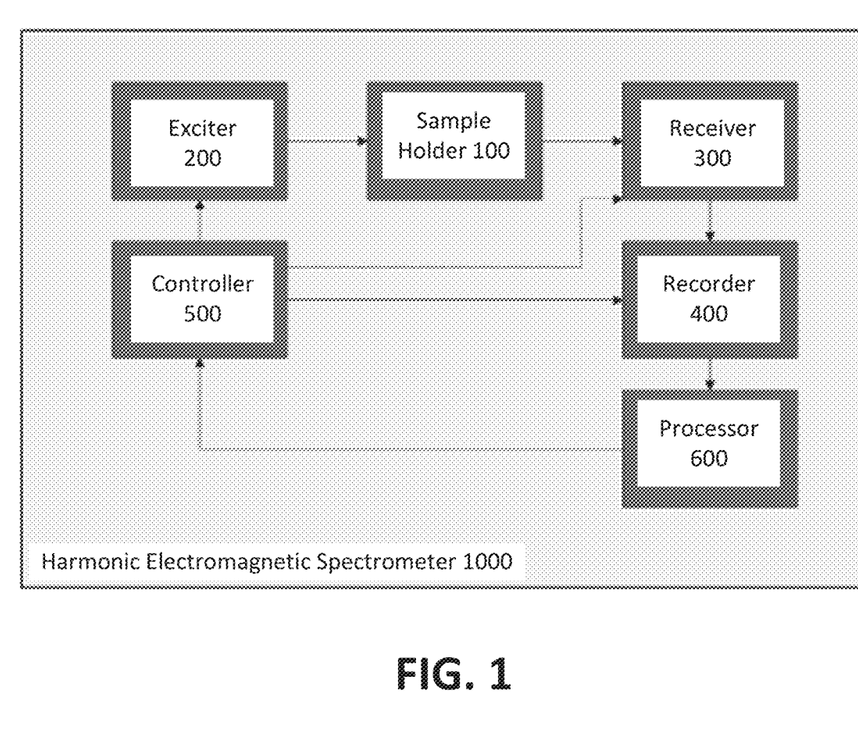
FIG. 1 is a schematic illustration of a harmonic electromagnetic spectrometer.

Referring to FIG. 1, a harmonic electromagnetic spectrometer 1000 (i.e., a non-destructive testing system) includes a sample holder 100, an exciter 200, a receiver 300, a recorder 400, a controller 500 and a processor 600. The harmonic electromagnetic spectrometer 1000 is configured to induce and record endogenous harmonic electromagnetic signals that characterize microstructural features in a sample.

The sample holder 100 is configured to fully or partially contain or support a sample to be analyzed in the harmonic electromagnetic spectrometer 1000. In some examples, the sample may be an ex vivo or in vivo biological tissue sample. However, the harmonic electromagnetic spectrometer 1000 is not limited in this regard. In other examples, any other type of sample may be used. For example, the sample may be conductive and/or contain charge-carrying particles (ions). In other examples in which the samples are non-conductive and/or do not contain charge-carrying particles, the sample may be immersed in an ionic solution (as will be discussed in further detail below with regard to FIG. 9). The sample holder 100 is made out of a non-conductive material that is resistant against corrosion and other chemical reactions. For example, the sample holder 100 may be made from plastics such as PTFE or HDPE, glass, or porcelain. The sample holder may be any shape. In some examples, described in further detail below, the sample holder 100 may be one of the structural components configured to contain or support the exciter 200 and the receiver 300.

As illustrated in the figures, the sample is placed in the sample holder 100, where the sample remains for the duration of the testing. However, placement of the sample is not limited in this regard. In other examples, the sample holder may include a flow chamber or tube through which the sample, a fluid in which the sample is to be immersed, or a fluid in which the sample is immersed may flow in and out of the testing apparatus. In such a configuration, measurements may be taken in pre-defined intervals during which there is no flow, or measurements may be taken continuously (i.e., during flow and when there is no flow). The fluid in which the sample is to be immersed or in which the sample is immersed may be, for example, a contrast agent used to facilitate detection of the microstructural features of an otherwise dry or solid sample.

The exciter 200 is configured to create an electric field across the sample that oscillates at a single frequency ($f_0$) with a narrow bandwidth ($\Delta f_0$), where $f_0 > \Delta f_0$. For example, $f_0$ may be greater than $\Delta f_0$ by one order of magnitude or more (e.g., one order of magnitude, two orders of magnitude, three orders of magnitude, etc.). In one, non-limiting example, $f_0$ may be 100 Hz, and $\Delta f_0$ may be 5 Hz. The frequency $f_0$ may be, for example, below 1 MHz. In other words, the frequency $f_0$ may be in the kHz range in a narrow, broad, or continuous spectrum. In some examples, $f_0 < \Delta f_0$ if a differential amplifier is used.

Figure 2:
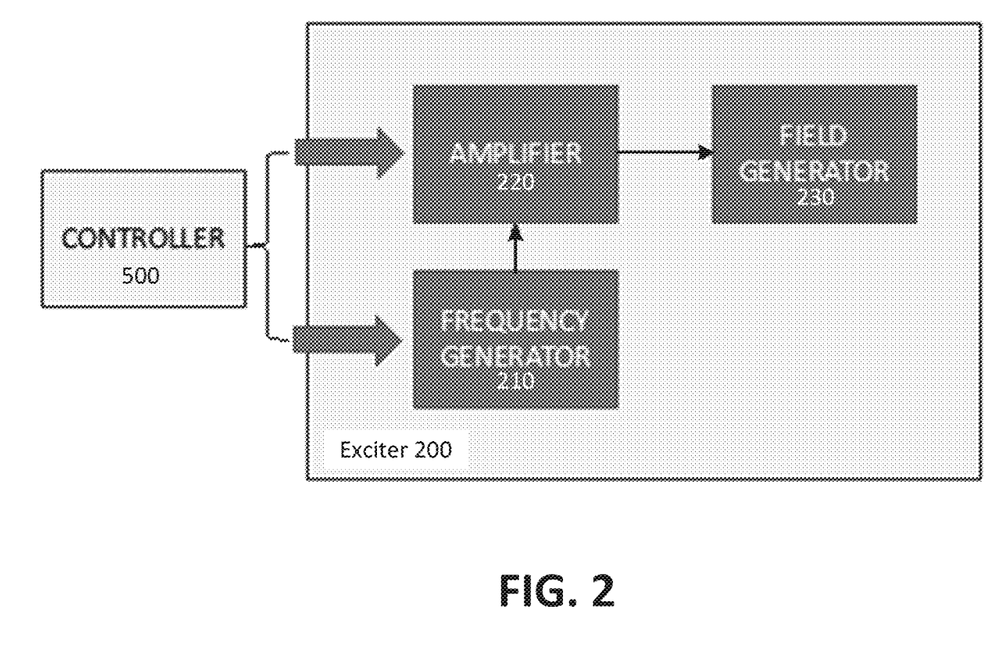
FIG. 2 is a schematic illustration of an exciter in the harmonic electromagnetic spectrometer of FIG. 1.

Referring to FIG. 2, the exciter 200 includes a frequency generator 210 configured to create a signal at a predetermined frequency $f_0$, an amplifier 220 configured to amplify the signal, and a field generator 230. The field generator 230 is configured to create an excitation field that ideally, in the area of the sample, is approximately spatially uniform in both amplitude and directionality. However, a non-uniform field can also be used at the expense of a reduced signal to noise ratio and or reduced accuracy or specificity. No externally applied static or switchable magnetic fields or magnetic field gradients are used to modulate/create the signal response.

Figure 8:
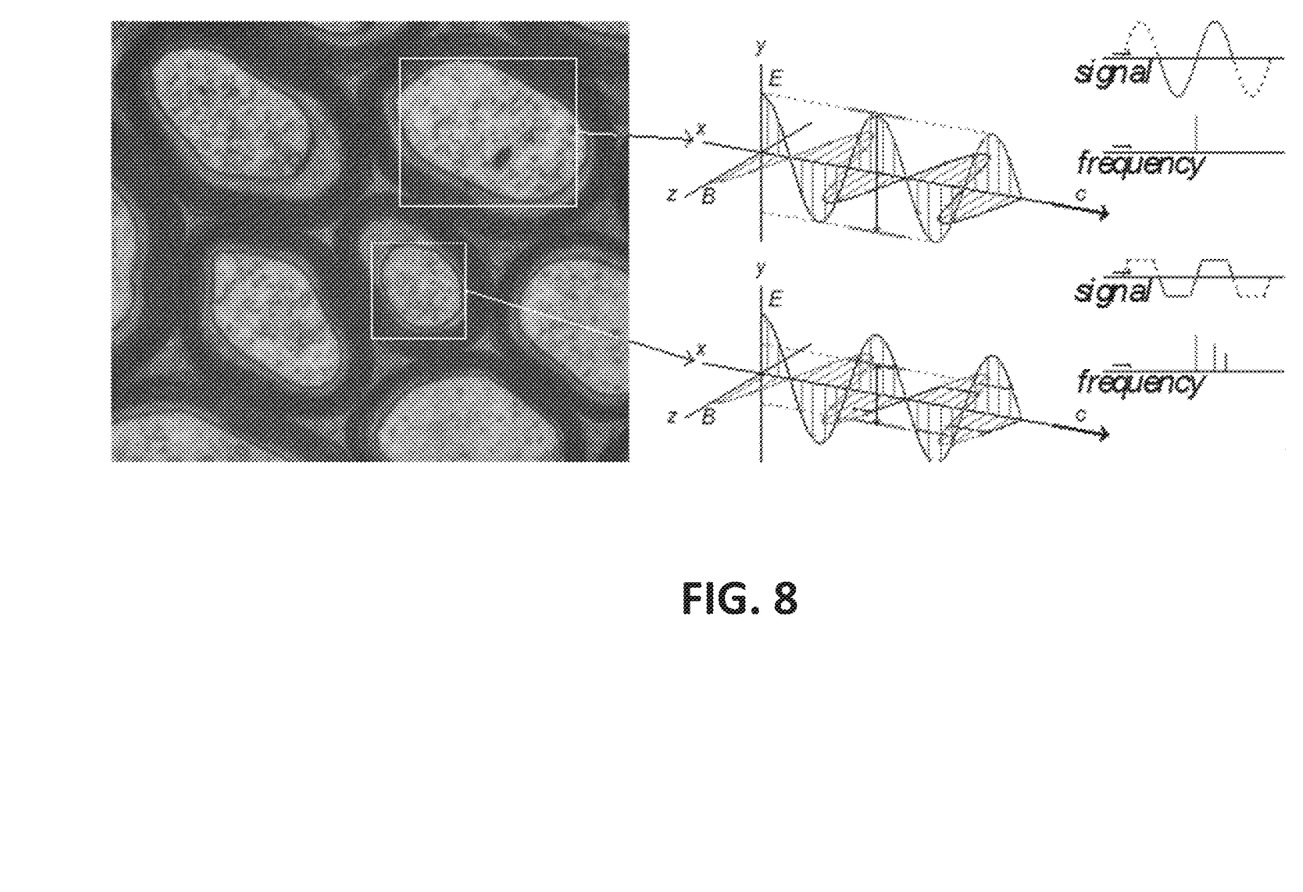

In the example of FIG. 8 (which will be described in further detail below), the excitation field generated by the field generator is sinusoidal. However, the harmonic electromagnetic spectrometer 1000 is not limited in this regard. In other examples, the excitation field or stimulus may have a non-sinusoidal waveform (e.g., square waveforms, triangle waveforms, sawtooth waveforms, spiked waveforms, trapezoidal waveforms, rectangular waveforms, etc.). Any oscillating excitation field may be used.

Figure 3:
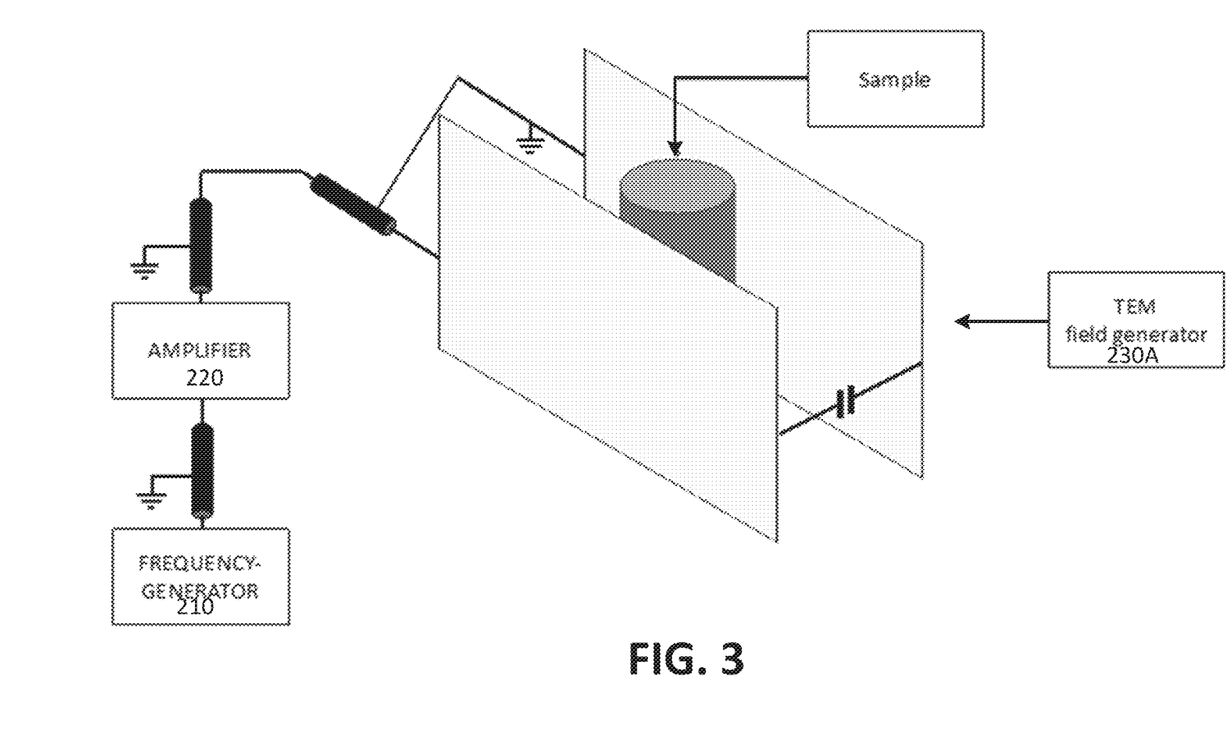
FIG. 3 is a schematic illustration of a transverse electromagnetic (TEM)-based electric field generator for use in the exciter of FIG. 2.
Figure 10:
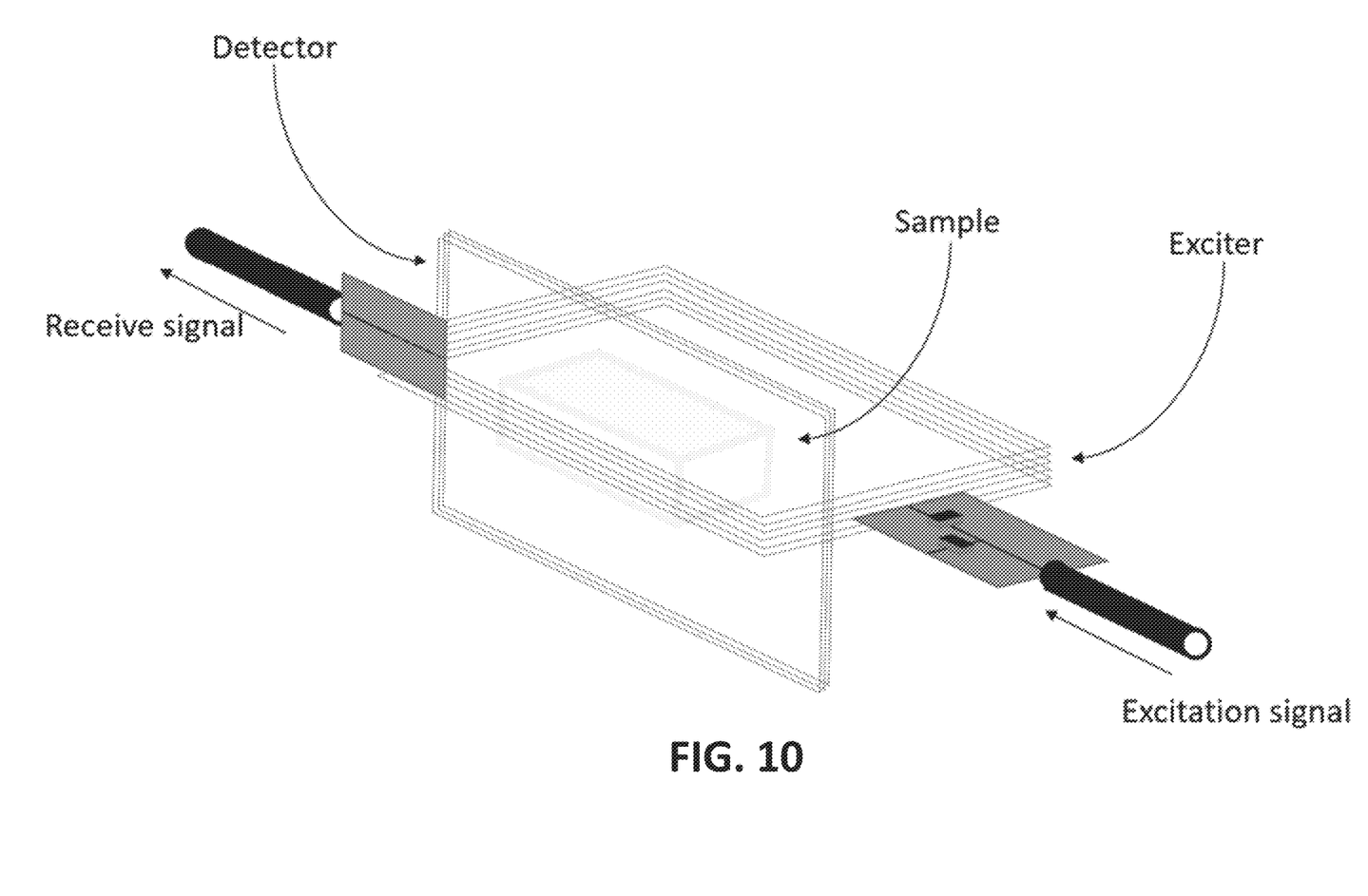
FIG. 10 is a schematic illustration of a harmonic electromagnetic spectrometer that includes a solenoid as the exciter, as an alternative to the transverse electromagnetic (TEM)-based electric field generator of FIG. 3.

FIG. 3 illustrates one exemplary embodiment of the field generator 230. In FIG. 3, the field generator 230 is provided in the form of a transverse electromagnetic (TEM) transmission line/resonator 230A. TEM is a mode of propagation where the electric and magnetic field lines are all restricted to directions normal (transverse) to the direction of propagation. When using a TEM transmission line/resonator 230A to generate the excitation field, the sample is placed between the signal carrying conductor and ground plane. One benefit of this setup is the creation of a uniform excitation field. Alternatively, a solenoid, loops, multi-turn loops or a loop antenna may be used as the exciter (see FIG. 10). The two plates adjacent to the sample in FIG. 3 may be part of the sample holder 100 itself.

Figure 4:
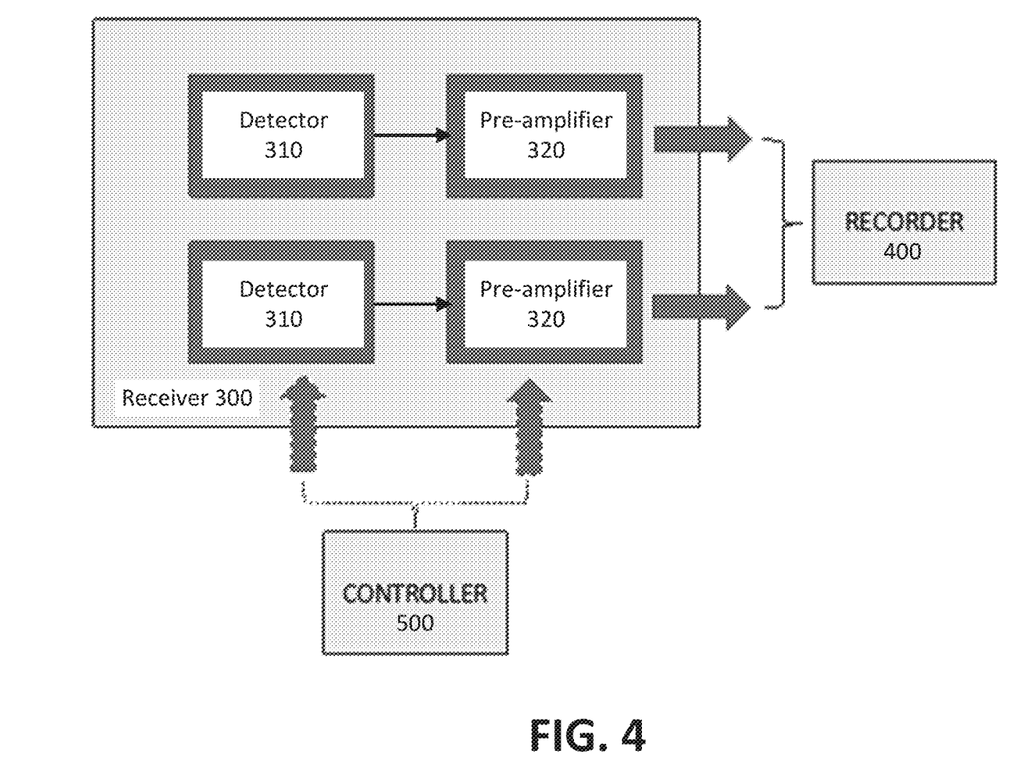
FIG. 4 is a schematic illustration of a receiver in the harmonic electromagnetic spectrometer of FIG. 1.

The receiver 300 is configured to capture a signal proportional to the reaction fields produced by the charged particles in the sample. Referring to FIG. 4, the receiver 300 may include one or more broadband or narrowband detectors 310, each accompanied by a suitable pre-amplifier 320. A detector is considered a broadband detector if the detector is designed to capture more than one harmonic. In particular, if the excitation frequency is "$f_0$" and the first harmonic "$f_1=2\ f_0$" and in general "$f_i=(i+1)\ f_0$", then the detector is a narrowband if "$f0>\Delta\ f0$," where $\Delta$ fi is the detector bandwidth. Otherwise, the detector is a broadband detector. The use of narrowband detectors versus broadband detectors are alternate modes of detection dependent upon the application of the system. Broadband detectors may measure multiple harmonics at once, while narrowband detectors may probe as many frequencies as detectors. The decision to use a narrowband detector instead of a broadband detector (and vice versa) may depend, for example, on whether the application requires complex spectra versus binary detection of presence/absence of one harmonic for commercial testing; whether one or a plurality of types of samples are being studied; cost restraints, etc.

The exciter 200 is configured to expose the sample to an electromagnetic field that oscillates at frequency $f_0$, while the receiver 300 is configured to simultaneously detect induced electromagnetic fields oscillating at least one frequency that is not equal to $f_0$. Each detector 310 provided in the receiver 300 is configured to detect a single frequency that is not equal to $f_0$. Although two detectors 310 are illustrated in FIG. 4, the receiver 300 is not limited in this regard. The receiver 300 may include any number of detectors 310, for example, 2, 3, 4, 5, 10, 15, 20, 30, 40, 50, 100, etc. detectors 310. In some examples, multiple receivers 300 may be used, where each receiver 300 includes one or more broadband or narrowband detectors 310.

In general, a plurality of detectors 310 are provided and configured to detect induced electromagnetic fields oscillating at a range of different frequencies to construct an induced harmonic electromagnetic spectrum to be used as a sensing modality. In some examples, the exciter 200 is configured to vary the frequency ($f_0$) of the excitation field used to induce the harmonic electromagnetic signal, while the receiver 300 is configured to simultaneous detect induced electromagnetic fields oscillating at least one frequency that is not equal to $f_0$. In such an example, multiple harmonic electromagnetic spectra are recorded (i.e., one spectrum for each excitation frequency).

The harmonic electromagnetic spectrum may be considered completed after a predetermined number of measurements are taken (e.g., record one measurement at frequencies f1, f2, f5, and f7), after measurements have been recorded for a predetermined period of time (e.g., record at frequencies f1, f2, f5, and f7 for 1 second), or after a predetermined signal-to-noise ratio (signal quality) is achieved (e.g., repeating measurements at f1, f2, f5, and f7 for 1 second until a certain signal-to-noise ratio is achieved), depending on the application. In one example, when transmitting at a single frequency, it may suffice to only test for the presence of a single harmonic. Suppose that a certain production process should create a product that is deemed to contain a defect in its microstructure when a certain harmonic is present, then it suffices to simply test for this harmonic. On the other hand, the presence of a certain harmonic may also confirm a desired aspect of the product. This approach may be valuable for quality control applications.

In another example in which an objective is to identify an unknown material, it may be necessary to record the harmonic spectrum at many different frequencies. In general, higher order harmonics are expected to be less efficient and more difficult to detect. In this case, a predetermined number of measurements may be taken at each frequency or measurements may be taken for predetermined periods of time at each frequency, depending on the unknown material. Because higher order harmonics are expected to show lower amplitudes (at least as a general rule looking over a large range of frequencies), it may be helpful to refine the spectrum by varying the transmit frequency. This way, additional harmonics may be studied without the loss of signal observed at the high frequencies associated with higher order harmonics. In other words, this could help refine the spectrum and help better distinguish certain materials.

The detectors 310 are configured to transform the electromotive force associated with the reactive fields into a detectable electric voltage or current. The electric voltage or current is then amplified by a respective pre-amplifier 320 before being sent to the recorder 400.

When a broadband detector 310 is used, its upper/lower cutoff frequency must be below/above the transmit frequency $f_0$ to avoid coupling to the exciter frequency. Alternatively, the detectors 310 can also be decoupled from the excitation field by manipulating their spatial orientation relative to the exciter 200 using a known geometrical decoupling technique. Broadband detectors may use a single recorder unit, in particular, a broadband record. In some examples, filters may optionally be used to block noise observed at certain frequencies.

Figure 5:
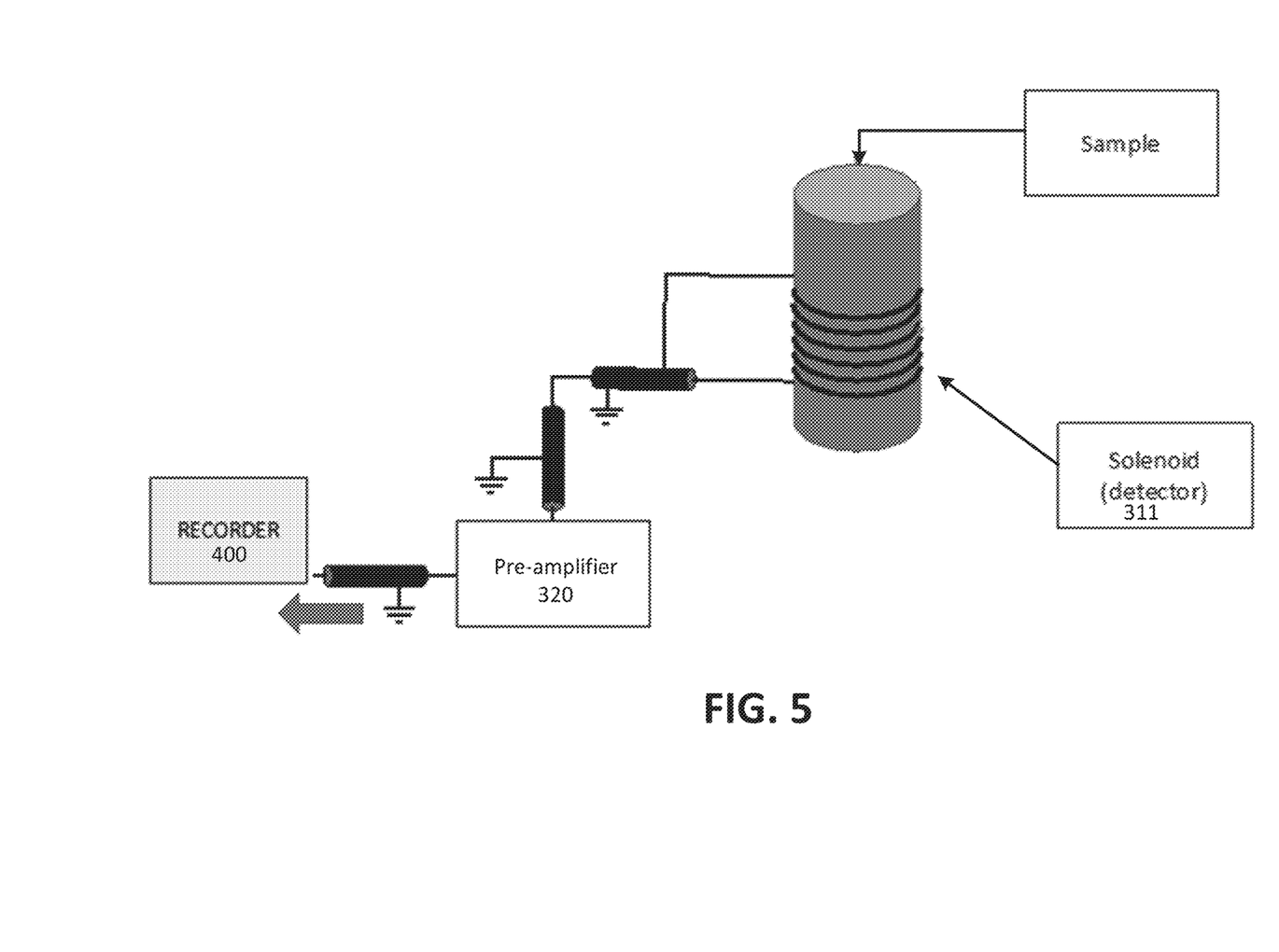
FIG. 5 is a schematic illustration of a solenoid narrowband detector for use in the receiver of FIG. 4.

When one or more narrowband detectors 310 are used, the detectors 310 must be tuned to the harmonic frequencies of the excitation field, i.e., $2 \times f_0$, $3 \times f_0$, $4 \times f_0$, etc. FIG. 5 illustrates an exemplary embodiment of a narrowband detector 310 in the form of a solenoid 311 wound about the sample or sample holder 100. In this example, the solenoid 311 may be tuned to double the excitation frequency. Each narrow bandwidth of each narrowband detector may minimize sample noise observed at other frequencies. However, additional recorders may be needed to collect all these signals at the same time. Alternatively, still using narrowband detectors, one could measure for a longer predetermined period of time and switch the recorder between detectors.

The system may include a plurality of detectors each configured to measure at the same or different excitation frequencies. In some examples, only narrowband detectors are used. In other examples, only broadband detectors are used. In further examples, a combination of narrowband and broadband detectors is used (e.g., at least one narrowband detector and at least one broadband detector). Combining both narrow and broadband detectors in a single setup, may provide additional versatility. For example, a quick broadband measurement may be performed to identify certain key frequencies of interest, which could then be refined using a tailored narrowband measurement.

Figure 6:
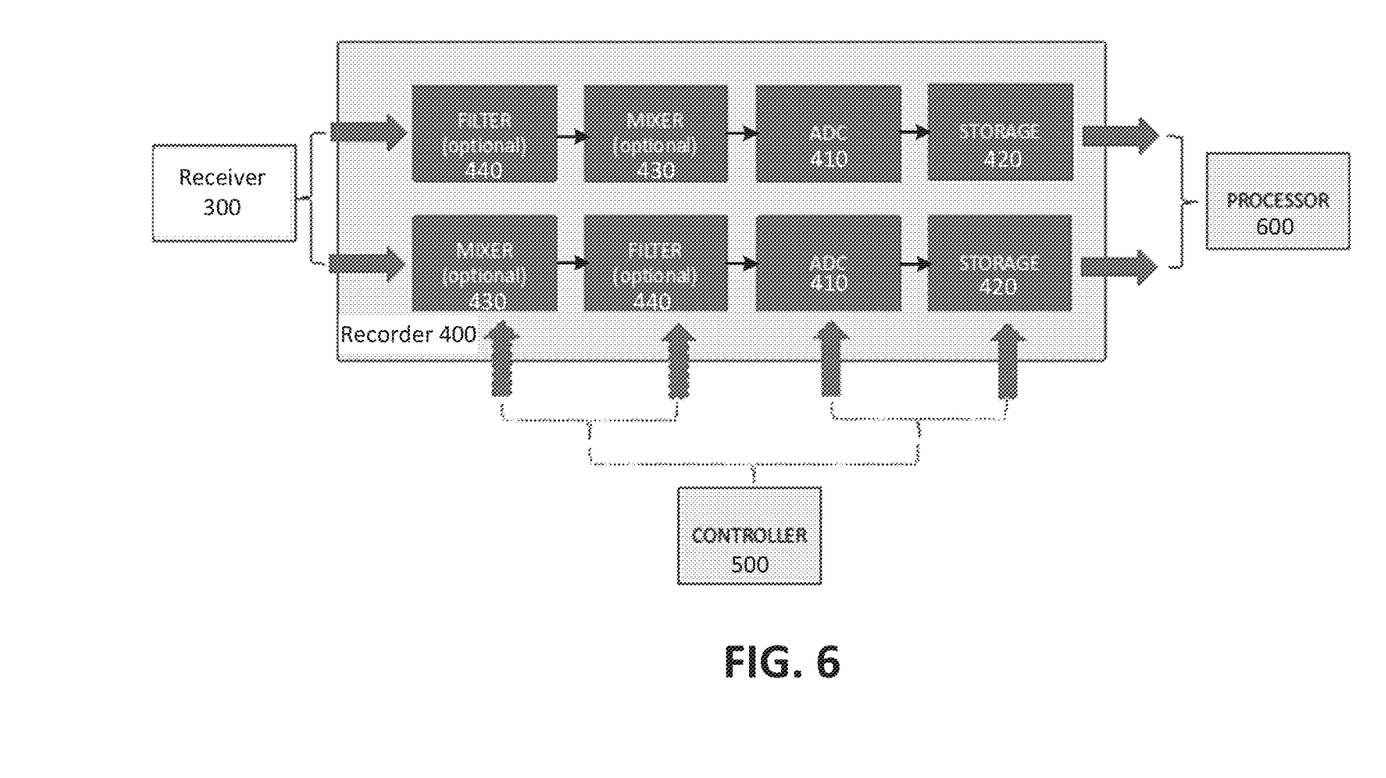
FIG. 6 is a schematic illustration of a recorder in the harmonic electromagnetic spectrometer of FIG. 1.

Referring to FIG. 6, in one exemplary embodiment, the recorder 400 includes one or more analog to digital converters (ADC) 410 and data storage systems 420 configured to store the measurements taken by the receiver 300 in a memory thereof. The memory may be, for example, a non-transitory memory. A mixer 430 may optionally be placed in the signal path before the ADC 410 to demodulate the frequency. The mixer 430 is an electrical circuit configured to produce a demodulated frequency at the sum and difference of the original frequencies received. The ADC 410 is configured to record a time-dependent signal amplitude, which can be transformed into a frequency spectrum by means of a Fourier transform. Alternatively, when the signals are obtained with one or more narrowband detectors 310, a rectifier (not illustrated) may be used such that the signal from each detector 310 may be integrated directly. In addition, the recorder 400 may also optionally contain frequency selective filters 440 configured to eliminate residual signal contamination from the exciter 200 or other electronic components. In examples including a frequency selective filter 440 and a mixer 430, the filter 440 may be provided upstream or downstream of the mixer 430. However, both the filter 440 and the mixer 430 are provided upstream of the ADC 410.

The controller 500 is programmed to coordinate the functions of the exciter 200, the receiver 300, and the recorder 400. In particular, the controller 500 is programmed to start and stop the exciter 200, set frequency or frequency sweep, and to start and stop the recorder 400. The recorder 400 may be set to stop recording after enough measurements are taken to achieve a desired signal quality/signal-to-noise ratio. During the non-destructive testing (measurement) the exciter 200, the receiver 300, and the recorder 400 may all be simultaneously active. The controller 500 is programmed to set the amplitude and frequency of the oscillating excitation field generated by the exciter 200. If the receiver 300 contains multiple detectors 310, the controller 500 may be further programmed to enable/disable individual detectors 310 independently of the other detectors 310. The controller 500 is also programmed to determine when and for how long the signals sent by the receiver 300 to the recorder 400 will be recorded. The controller 500 may be programmed dynamically by the processor 600 or a separate computer.

Figure 7:
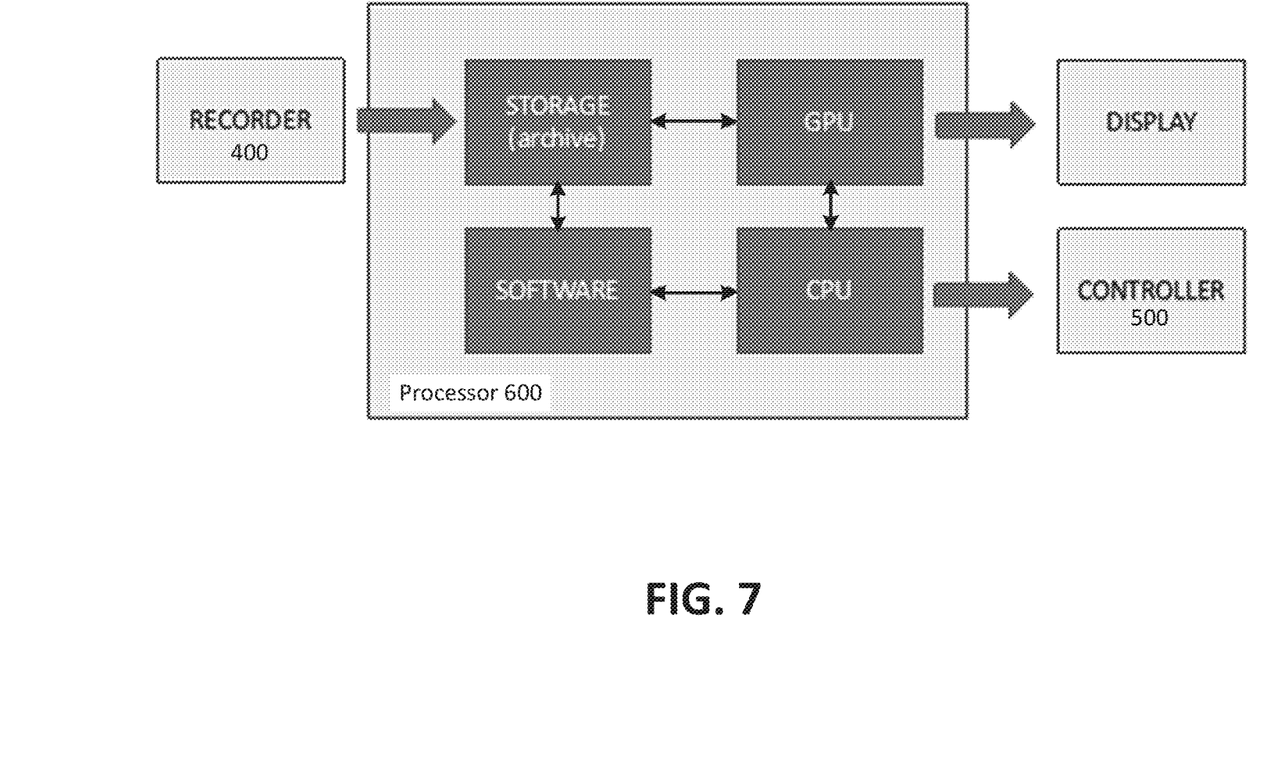
FIG. 7 is a schematic illustration of a processor in the harmonic electromagnetic spectrometer of FIG. 1.

Referring to FIG. 7, the processor 600 includes a central processing unit (CPU) and a graphics processing unit (GPU) configured to render images, animations and/or video on a display to allow a user to archive and manipulate the recorded data received from the recorder 400. In particular, each non-destructive test may include multiple sample measurements. For example, a given sample may be excited using electric fields oscillating with various amplitudes and at different frequencies. In each of these cases, the observed reactive fields may be recorded at multiple frequencies. This collection of measurements forms a characteristic signature of the sample, which will be referred to as the harmonic electromagnetic spectrum. The processor 600 includes software that allows a user to manipulate and display the harmonic electromagnetic spectra and perform operations necessary for its characterization and interpretation (e.g., comparing the measured signal and a library of pre-measured samples with known properties, origins, etc.). The processor 600 further includes a storage configured to store the data received from the recorder in a memory. The memory may be a non-transitory memory.

Harmonic electromagnetic spectra can be used to infer detailed microscopic structural properties of the sample. The harmonic electromagnetic spectra can be interpreted in at least three distinct ways. First, if a suitable physical, chemical, and/or biological model is available, the degrees of freedom in the model may be fitted to the measured harmonic electromagnetic spectra, thus fully characterizing the effective microscopic obstructions in the sample. Second, in the absence of a tractable analytical solution, the measured harmonic electromagnetic spectra may be matched to the entries in a dictionary of numerically simulated harmonic electromagnetic spectra. In this case, the parametrization of the simulation that corresponds to the best match identifies all (or a subset) of the sample properties. Third, the measured harmonic electromagnetic spectra may be correlated to previous recordings. Such measurements may be used for quality control or classification. For example, in one exemplary embodiment, production samples that show a deviation from the standard harmonic electromagnetic spectra may be considered inadequate and discarded for quality assurance/control. In another exemplary embodiment, samples may be classified based on their similarity to one or more previously measured samples. In other words, the classification or identification of samples may be based on the presence or lack of harmonic electromagnetic signals or spectra.

Referring to FIG. 8, endogenous harmonic electromagnetic signals are expected to be found in biological tissues. When exposed to oscillating electromagnetic fields, charged particles in a conductive medium, such as ions in a cell or in vascular or interstitial fluid, will move in response to the applied fields. When their path of motion is unobstructed, these particles will induce reaction fields at the same frequency as the incident fields. However, if their motion is constrained by microstructural features in the sample (e.g. in the small axon at bottom of FIG. 8), the ions' induced motion pattern will be truncated, resulting in truncated reaction fields, with substantial frequency content at harmonics of the incident field frequency. In other words, the observation of truncated reaction fields can be interpreted as a marker for microscopic restrictions in the local ion environment.

Figure 9:
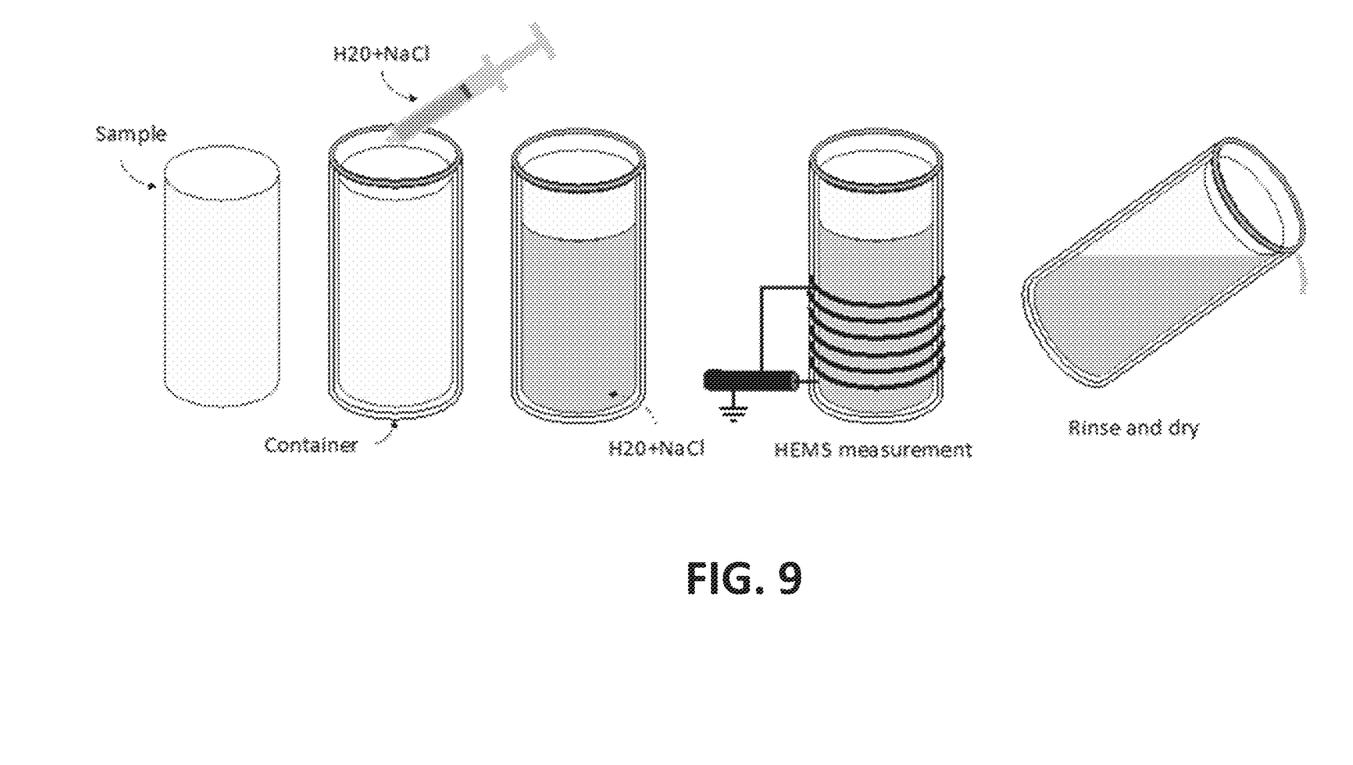
FIG. 9 is a schematic illustration of an example setup for using the harmonic electromagnetic spectrometer of FIG. 1 where a sample is submerged in a sample holder containing an ion solution as a contrast agent.

Referring to FIG. 9, complex permeable samples lacking charged particles or other constituents that respond appropriately to applied electromagnetic fields may also be analyzed with harmonic electromagnetic spectroscopy using a contrast agent. For example, in one exemplary embodiment, a sample containing microstructural features may be immersed in a conductive solution used as a contrast agent. In some examples, the conductive solution may be any liquid containing mobile ions or charge carriers such as salt water. Once the sample is saturated with the conductive solution, the dissolved ions may be used to probe the microstructure using the harmonic electromagnetic spectroscopy techniques described above. When the measurement is finished, the sample may be returned to its original condition by washing out the contrast agent and allowing the sample to dry. In other words, the harmonic electromagnetic spectroscopy technique is non-destructive.

Another embodiment relates to a method of generating a harmonic electromagnetic spectrum for non-destructive testing of a sample. The method includes placing a sample in a sample holder or otherwise bringing the sample into the vicinity of the testing apparatus; generating a time-varying electromagnetic field across the sample; detecting distortions of the waveform of the electromagnetic field; and constructing an induced harmonic electromagnetic spectrum based on the detected waveform distortions. Time dependent modulation of the phase and amplitude of the harmonic spectral components as a function of the excitation pulse shape may provide new or more comprehensive information about the sample. In some examples, the distortions are only detected during application of the excitation field. In other examples, the distortions are detected at all times (i.e., when the excitation field is applied and when the excitation field is not applied).

In any of the embodiments described above, instead of placing the sample in the sample holder, the method may include bringing the sample into the vicinity of the testing apparatus. This may include bringing the testing apparatus to the sample, for example, in a handheld or wearable configuration, as opposed to surrounding the sample by the testing apparatus in a sample holder. The testing apparatus may include an exciter configured to generate an oscillating electromagnetic field across the sample that operates with at least one predetermined excitation frequency and a receiver configured to detect harmonic electromagnetic signals resulting from induced electromagnetic fields oscillating with at least one frequency that is not equal to the at least one predetermined excitation frequency. The testing apparatus may further include a recorder configured to record the harmonic electromagnetic signals, and a processor programmed to construct an induced harmonic electromagnetic spectrum based on the harmonic electromagnetic signals. In some aspects, the exciter, the receiver, the recorder, and the processor are all be contained in the handheld or wearable configuration. In other aspects, only the exciter is contained in the handheld or wearable configuration, while the receiver, the recorder and the processor are external to the handheld or wearable configuration. In further aspects, only the exciter and the receiver are contained in the handheld or wearable configuration, while the recorder and the processor are external to the handheld or wearable configuration. In even further aspects, only the exciter, the receiver, and the recorder are contained in the handheld or wearable configuration, while the processor is external to the handheld or wearable configuration.

The harmonic electromagnetic spectrometer 1000 and methods of acquiring harmonic electromagnetic signals or spectra described above may be used in various applications such as materials testing, medical devices, precision measurement equipment, handheld and wearable devices, etc. For example, the harmonic electromagnetic spectrometer 1000 and method of acquiring harmonic electromagnetic signals or spectra described above may be used for product, quality-control during the manufacturing of products, as a diagnostic tool for trouble shooting and equipment repair, or as a medical diagnostic tool.

As discussed above, when exposed to oscillating electromagnetic fields of moderate frequency, charged particles in a conductive medium, such as ions in a solvent, will move in response to those fields, and will induce reaction fields at the same frequency as the incident fields. This behavior is a manifestation of Ohm's law. However, if the motion of charge carriers is constrained by microstructural features of their surroundings, their induced motion pattern will be truncated, resulting in similarly truncated reaction field oscillations. Such truncated oscillations, or other nonlinearities, result in characteristic patterns of harmonics at multiples of the incident frequency, which allow for the acquisition/creation and evaluation of induced harmonic electromagnetic spectra. The harmonic electromagnetic spectra may be used as a new sensing modality. Historically, biological tissues have been assumed to be Ohmic in bulk, ignoring their complex cellular composition and even their capacity for spontaneous electrical activity. Typically, the electrical properties (e.g., conductivity, permittivity, etc.) of biological tissues are assumed to be linear. In the induced harmonic electromagnetic spectra, tissues and other complex materials will exhibit previously unseen non-linearities, which will enable their microstructural features to be characterized, in situ and/or in vivo.

Evaluating the harmonic electromagnetic spectra of a sample provides a direct and flexible measurement of microscopic restrictions. The harmonic electromagnetic spectra are also sensitive to other forms of non-linear electromagnetic response, such as voltage-sensitive changes in conductivity associated with cellular activity, which are expected to differ in spectral signature from the restriction-based signatures (see FIG. 8). It may also be possible to localize the harmonic electromagnetic signals with high resolution (e.g., through appropriate spatial modulation of the applied fields). The harmonic electromagnetic spectrometer does not require expensive and bulky apparatuses such as the superconductive magnets needed to perform NMR or MRI. In fact, desktop, handheld, or even wearable harmonic electromagnetic spectrometers may be used to impose electromagnetic fields and measure harmonic electromagnetic responses. The harmonic electromagnetic effect has the potential to generate a plethora of affordable measurement techniques that could enable new research across a wide range of fields.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the harmonic electromagnetic spectrometer as shown in the various exemplary embodiments is illustrative only. Additionally, any element disclosed in one embodiment may be incorporated or utilized with any other embodiment disclosed herein.

What is claimed is:

1. An apparatus for non-destructive testing of a sample comprising:
    a sample holder configured to fully or partially contain or support the sample;
    an exciter configured to generate an oscillating electromagnetic field across the sample that operates with at least one predetermined excitation frequency;
    a receiver configured to detect harmonic electromagnetic signals resulting from induced electromagnetic fields oscillating with at least one frequency that is not equal to the at least one predetermined excitation frequency;
    a recorder configured to record the harmonic electromagnetic signals; and
    a processor programmed to construct an induced harmonic electromagnetic spectrum based on the harmonic electromagnetic signals.

2. The apparatus of claim 1, wherein
    the receiver comprises a plurality of detectors; and
    each detector is configured to detect harmonic electromagnetic signals at frequencies that are not equal to the at least one predetermined excitation frequency of the oscillating electromagnetic field used to induce the harmonic electromagnetic signals.

3. The apparatus of claim 2, wherein
    the receiver comprises a first detector configured to detect harmonic electromagnetic signals resulting from an induced electromagnetic field oscillating at a first frequency that is not equal to the at least one predetermined excitation frequency;

the receiver comprises a second detector configured to detect harmonic electromagnetic signals resulting from an induced electromagnetic field oscillating at a second frequency that is not equal to the at least one predetermined excitation frequency; and
the first frequency and the second frequency are not equal.

4. The apparatus of claim 1, wherein the sample holder is configured to contain a contrast agent in which the sample is immersed.

5. The apparatus of claim 1, wherein the harmonic electromagnetic signals are endogenous to the sample.

6. The apparatus of claim 1, wherein the sample holder comprises a flow chamber or tube through which the sample, a fluid in which the sample is to be immersed, or a fluid in which the sample is immersed is configured to flow.

7. A method of generating a harmonic electromagnetic spectrum for non-destructive testing of a sample, the method comprising:
placing a sample in a sample holder or otherwise bringing the sample into the vicinity of a testing apparatus;
generating an oscillating electromagnetic field across the sample that operates with at least one predetermined excitation frequency;
detecting harmonic electromagnetic signals resulting from induced electromagnetic fields oscillating with at least one frequency that is not equal to the at least one predetermined excitation frequency; and
constructing an induced harmonic electromagnetic spectrum based on the harmonic electromagnetic signals.

8. The method of claim 7, wherein
detecting the harmonic electromagnetic signals comprises:
detecting harmonic electromagnetic signals resulting from an induced electromagnetic field oscillating at a first frequency that is not equal to the at least one predetermined excitation frequency; and
detecting harmonic electromagnetic signals resulting from an induced electromagnetic field oscillating at a second frequency that is not equal to the at least one predetermined excitation frequency;
the first frequency and the second frequency are not equal; and
the induced harmonic electromagnetic spectrum is constructed based on the harmonic electromagnetic signals oscillating at the first frequency and the harmonic electromagnetic signals oscillating at the second frequency.

9. The method of claim 7, further comprising constructing a plurality of induced harmonic electromagnetic spectra, wherein an induced harmonic electromagnetic spectrum is constructed for each predetermined excitation frequency at which the oscillating electromagnetic field operates.

10. The method of claim 7, further comprising fitting the induced harmonic electromagnetic spectrum to degrees of freedom in a physical or biochemical model to identify structural features in the sample.

11. The method of claim 7, further comprising:
comparing the induced harmonic electromagnetic spectrum to a plurality of simulated harmonic electromagnetic spectra;
selecting a simulated harmonic electromagnetic spectrum that most closely matches the induced harmonic electromagnetic spectrum; and
inferring at least one sample property based on a property associated with the selected simulated harmonic electromagnetic spectrum.

12. The method of claim 7, further comprising:
acquiring a standard harmonic electromagnetic spectrum for a product with known properties;
comparing the induced harmonic electromagnetic spectrum to the standard harmonic electromagnetic spectrum; and
determining that the sample is inadequate or flawed if the induced harmonic electromagnetic spectrum deviates from the standard harmonic electromagnetic spectrum by more than an acceptable tolerance.

13. The method of claim 7, further classifying or identifying samples based on a presence or lack of harmonic electromagnetic signals in the induced harmonic electromagnetic spectrum.

14. The method of claim 7, wherein the harmonic electromagnetic signals are endogenous to the sample.

15. The method of claim 7, wherein the harmonic electromagnetic signals are produced by a contrast agent introduced into the sample.

16. The method of claim 7, wherein the sample comprises ex vivo biological tissue or in vivo biological tissue.

17. The method of claim 7, further comprising detecting induced electromagnetic fields oscillating at a range of different frequencies to construct the induced harmonic electromagnetic spectrum.

18. The method of claim 7, further comprising:
varying the at least one predetermined excitation frequency of the excitation field used to induce the harmonic electromagnetic signals; and
detecting the harmonic electromagnetic signals resulting from induced electromagnetic fields oscillating at least one frequency that is not equal to the at least one predetermined excitation frequency.

19. The method of claim 18, further comprising constructing multiple induced harmonic electromagnetic spectra, wherein one induced harmonic electromagnetic spectrum is obtained for each predetermined excitation frequency of the excitation field used to induce the harmonic electromagnetic signals.

20. A method of generating a harmonic electromagnetic spectrum for non-destructive testing of a sample, the method comprising:
placing a sample in a sample holder or otherwise bringing the sample into the vicinity of a testing apparatus;
collecting a first set of measurements by
generating an excitation field across the sample that operates at a first single predetermined frequency;
detecting harmonic electromagnetic signals resulting from induced electromagnetic fields oscillating at least one frequency that is not equal to the first single predetermined frequency; and
constructing a first induced harmonic electromagnetic spectrum based on the harmonic electromagnetic signals; and
collecting a second set of measurements by
generating an excitation field across the sample that operates at a second single predetermined frequency different from the first single predetermined frequency;
detecting harmonic electromagnetic signals resulting from induced electromagnetic fields oscillating at least one frequency that is not equal to the second single predetermined frequency; and
constructing a second induced harmonic electromagnetic spectrum based on the harmonic electromagnetic signals.

* * * * *